(12) United States Patent
Pignede et al.

(10) Patent No.: US 10,738,329 B2
(45) Date of Patent: Aug. 11, 2020

(54) USE OF MCM7 TO OBTAIN ACETIC ACID-RESISTANT YEAST STRAINS

(71) Applicant: LESAFFRE et COMPAGNIE, Paris (FR)

(72) Inventors: Georges Pignede, Marcq en Baroeul (FR); Thomas Desfougeres, Dissay (FR)

(73) Assignee: LESAFFRE et COMPAGNIE, Paris (FR)

( * ) Notice: Subject to any disclaimer, the term of this patent is extended or adjusted under 35 U.S.C. 154(b) by 0 days.

(21) Appl. No.: 16/331,077

(22) PCT Filed: Aug. 31, 2017

(86) PCT No.: PCT/FR2017/052316
§ 371 (c)(1),
(2) Date: Mar. 6, 2019

(87) PCT Pub. No.: WO2018/046820
PCT Pub. Date: Mar. 15, 2018

(65) Prior Publication Data
US 2019/0367951 A1    Dec. 5, 2019

(30) Foreign Application Priority Data
Sep. 8, 2016 (FR) ..................................... 16 58370

(51) Int. Cl.
| | | |
|---|---|---|
| C12P 7/06 | (2006.01) | |
| C12P 7/10 | (2006.01) | |
| C12N 1/36 | (2006.01) | |
| C12N 1/16 | (2006.01) | |
| C07K 14/395 | (2006.01) | |
| C12N 1/18 | (2006.01) | |
| C12N 15/81 | (2006.01) | |

(52) U.S. Cl.
CPC ............. *C12P 7/06* (2013.01); *C07K 14/395* (2013.01); *C12N 1/18* (2013.01); *C12N 15/81* (2013.01)

(58) Field of Classification Search
CPC ..... C12N 1/36; C12N 1/16; C12P 7/06; C12P 7/10; C12R 1/865
See application file for complete search history.

(56) References Cited

FOREIGN PATENT DOCUMENTS

| WO | WO-2010/000464 A1 | 1/2010 |
|---|---|---|
| WO | WO-2012/072793 A1 | 6/2012 |
| WO | WO-2013/178915 A1 | 12/2013 |

OTHER PUBLICATIONS

Akada et al., Screening and identification of yeast sequences that cause growth inhibition when overexpressed (Abstract Only), *Mol. Gen. Genet.* 254:267-74 (1997).
Akada et al., Sets of integrating plasmids and gene disruption cassettes containing improved counter-selection markers designed for repeated use in budding yeast (Abstract Only), *Yeast.* 19:393-402.
Fitch et al., Mcm7, a subunit of the presumptive MCM helicase, modulates its own expression in conjunction with Mcm1, *J. Biol. Chem.* 278:25408-16 (2003).
Internatioanl Search Report and Written Opinion, PCT/FR2017/052316 (dated Oct. 26, 2017).
Kawahata et al., A positive selection for plasmid loss in *Saccharomyces cerevisiae* using galactose-inducible growth inhibitory sequences (Abstract Only), *Yeast.* 15:1-10 (1999).
Lander et al., Mapping mendelian factors underlying quantitative traits using RFLP linkage maps (Abstract Only), *Genetics.* 121:185-99 (1989).
Lee et al., Transcriptome analysis of acetic-acid-treated yeast cells identifies a large set of genes whose overexpression or deletion enhances acetic acid tolerance, *Appl. Microbiol. Biotechnol.* 99:6391-6403 (2015).
Mira et al., Genomic expression program involving the Haa1p-regulon in *Saccharomyces cerevisiae* response to acetic acid, *OMICS.* 14:587-601 (2010).
Mira et al., Identification of a DNA-binding site for the transcription factor Haa1, required for *Saccharomyces cerevisiae* response to acetic acid stress (Abstract Only), *Nucleic Acids Res.* 39:6896-907 (2011).
NCBI Database Accession No. 852501, MCM7 mini-chromosome maintenance complex protein 7 [ *Saccharomyces cerevisiae* S288C ], Sep. 9, 2018.
NCBI Database Accession No. GCA-000146045.2, *Saccharomyces cerevisiae* S288C (baker's yeast), Apr. 18, 2011.
NCBI Database Accession No. NC_001134.7, *Saccharomyces cerevisiae* S288c chromosome II, complete sequence, Dec. 23, 2010.
Parts et al., Revealing the genetic structure of a trait by sequencing a population under selection (Abstract Only), *Genome Res.* 21:1131-8 (2011).

*Primary Examiner* — Maryam Monshipouri
(74) *Attorney, Agent, or Firm* — Marshall, Gerstein & Borun LLP

(57) ABSTRACT

The invention concerns the use of the MCM7 gene to confer resistance to an organic acid, preferably acetic acid, to a yeast strain during glucose fermentation.

14 Claims, 5 Drawing Sheets
Specification includes a Sequence Listing.

A/

B/

USE OF MCM7 TO OBTAIN ACETIC ACID-RESISTANT YEAST STRAINS

CROSS REFERENCE TO RELATED APPLICATIONS AND INCORPORATION BY REFERENCE OF MATERIAL SUBMITTED ELECTRONICALLY

This application is a U.S. National Stage of International Application No. PCT/FR2017/052316, filed Aug. 31, 2017, which claims the benefit of French Patent Application No. 1658370, filed Sep. 8, 2016, the entire contents of each of which are fully incorporated herein by reference.

A Sequence Listing, which is a part of the present disclosure, is submitted concurrently with the specification as a text file. The name of the text file containing the Sequence Listing is "53904_SubSeqlisting.txt." The Sequence Listing was created on Apr. 9, 2019, and is 1,059,363 bytes in size. The subject matter of the Sequence Listing is incorporated herein in its entirety by reference.

FIELD OF THE INVENTION

The present invention relates to the use of regulation for the expression of the MCM7 gene to confer resistance to an organic acid, advantageously acetic acid, to a yeast strain during glucose fermentation. Accordingly, the presence, at least at an allele, of a binding site for the transcription regulator Haa1p upstream of the MCM7 gene would induce its expression, which translates by increased resistance to the organic acid.

Moreover, the present invention offers a method allowing the genotypic selection of a yeast strain resistant to an organic acid, advantageously acetic acid, during the glucose fermentation. In the same way, the invention allows for substantial optimization of the yielded yeast strains resistant to an organic acid, advantageously acetic acid, based on the genotypic selection of the spores.

BACKGROUND OF THE INVENTION

The capacity of genetically modified yeasts to ferment diverse substrates makes them a tool of choice in diverse industrial processes, particularly in the production of ethanol from lignocellulose biomass. Alcoholic fermentation is the process yeasts use in anaerobic media during which sugars are transformed into alcohol. The yeast *Saccharomyces cerevisiae*, also know as "baker's yeast," remains the microorganism used most often for alcoholic fermentation.

However, some fermentation inhibitors are found naturally in these substrates and negatively impact ethanol production. This is in particular the case for weak organic acids, particularly for acetic acid, a degradation product of hemicellulose. When yeasts are confronted with the presence of organic acid in their environment, they block their cellular cycle to be able to prepare to react to this new abiotic stress. The fermentation only starts once the cellular resistance machinery is in place. The presence of a weak organic acid accordingly has the consequence of delaying the initiation of the fermentation on glucose, thereby increasing production costs.

The problem related to acetic acid is all the more crucial since it is a very powerful inhibitor for alcoholic fermentation by yeasts and it is found in high concentrations in some fermentation media.

Various means have been described to attempt to counter the effect of fermentation inhibitors, such as for instance detoxifying the fermentation medium, or adapting yeasts to fermentation inhibitors by acclimation or genetic modification. In the case of acetic acid, detoxifying the fermentation medium is a difficult option to implement, particularly industrially. It is therefore necessary to attempt to modify the yeasts themselves.

In this context, the acclimation of yeasts can be achieved by adding the inhibitor into the culture medium, preferably at increasing doses. However, it has been observed that yeast adaptation according to this method is only transient, and disappears quickly when they are again cultivated in a medium devoid of inhibitor. So the method proves to be of little industrial interest, as there phenotypically stable strains are necessary.

In the case of sensitivity to acetic acid, only the genetic modification of yeasts can therefore be envisaged. This can be done either by modification by genetic engineering, targeting specific genes, or classically by crossing strains of interest. Currently, the molecular mechanisms related to the sensitivity or on the contrary the resistance to acetic acid are poorly understood, and insufficient for the methods targeted by genetic engineering.

Accordingly, the method of choice to improve resistance to acetic acid remains yielding yeasts by crossing. However, even though some methods have yielded acetic-acid resistant yeast strains, these are by definition random and cannot guarantee success.

Document WO 2013/178915 describes crossing processes for yeast strains that allow the production of yeasts that can metabolize glucose and are acetic-acid resistant. This method consists in crossing the yeast strain filed at the CNCM under the number I-4538 with the yeast strain filed at the CNCM under the number I-4627, then in selecting a hybrid that can metabolize xylose and, independently, resist acetic acid during the fermentation of glucose.

This hybridization method relies on the capacity of yeasts to reproduce either asexually, or sexually, according to the culture conditions in particular.

Yeast *S. cerevisiae* is an organism with a haplodiplontic reproductive cycle, i.e. an organism capable of actively multiplying both in the haploid and the polyploid, for example diploid, state.

As long as the medium is favorable, polyploid yeasts are capable of vegetative multiplication by sprouting giving rise to polyploid yeasts. In the case of a medium poor in nitrogen-containing nutrients and containing only a non-fermentable carbon source (for example glycerol, acetate, etc.), the heterozygote cells for the Mat locus enter into meosis and form yeasts having lower ploidy (spores or segregants) by a mechanism called sporulation.

Segregants can multiply by sprouting, giving yeasts having the same genome. Among haploid yeasts two opposing sexual signs are distinguished, called MATa and MATα. Two haploid spores with opposite sexual type can fertilize to yield a diploid yeast.

The haplodiplontic cycle for *S. cerevisiae* has been widely used to cross sexually compatible segregants (MATa and MATα), particularly in the method called random recombination from mass sporulation and hybridization. In a classic manner, two parental diploid strains (different from the genomic point of view) are used. The sporulation of parental diploid strains is typically induced by cultivating them in conditions where the nitrogen supply is limited and only in the presence of a non-fermentable carbon source. The meiosis operating during this step leads to a genetic cross-fertilization, creating spores with varied genotype. The spores (haploid) obtained for each of the parental strains are then put in contact, to produce diploid (hybrid) strains by fusion. This last step is called the hybridization step.

This method is interesting in that it allows the creation of genetic cross-fertilization from which interesting phenotype traits can emerge. It does however require a step of selecting hybrids on the basis of desired phenotype traits. As an example, in the case of strictly diploid parental strains each presenting a phenotype trait borne by 10 genes, the probability of obtaining the hybrid of interest is estimated at $1/2.097.10^6$. The final selection step is tedious, long and expensive, especially.

Therefore an obvious need exists for improved production methods for acetic-acid resistant yeast strains.

DESCRIPTION OF THE INVENTION

The inventors have identified that the yeast strains of *S. cerevisiae* capable of having expression of MCM7 induced by an organic acid, particularly acetic acid, have a phenotype of resistance to this organic acid. As shown in the experimental section, the growth of these strains and their capacity to ferment the glucose in a medium rich in acetic acid are improved.

In a particularly interesting manner, the inventors have determined that the expression of MCM7 in these strains can be induced by acetic acid. In addition it appears that this expression of MCM7, induced by acetic acid, is mediated by the transcription factor Haa1p. This is particularly surprising, given that MCM7 is not known as being a gene regulated by Haa1p. Accordingly, the work of Mira and collaborators published in 2010 (Mira et al, 2010, OMICS, 14: 587-601) proposes a list of genes regulated by Haa1p in the strain BY4741, which does not include MCM7. The inventors did establish though that in the strains of *S. cerevisiae* that resist acetic acid, the region upstream of the MCM7 coding gene comprises a motif known to be a binding site for Haa1p. Without being bound to any theory, the presence of this binding site for Haa1p would be the fruit of single-nucleotide polymorphism (SNPs).

On the basis of these elements, the inventors have developed selection and production methods for acetic-acid resistant strains of *S. cerevisiae*.

Definitions

The term "yeast strain" denotes in the sense of the invention a yeast population strictly identical from a genetic point of view. This encompasses both strains referred to as laboratory strains and those referred to as industrial strains. This term is to be differentiated from the term "yeast," a yeast being obtained by the culture of a strain as defined above. In the context of the invention, "yeast" is understood as a commercial product obtained by implementation of a production method for a yeast strain. Thus, yeasts having different properties can be obtained from a single strain, where these differences are connected with the production method implemented.

In the meaning of the invention, a "segregant" is the product of the meiosis of a yeast strain, regardless of the ploidy level of said yeast. In the remainder of the application, the terms "segregant" and "spore" can be used interchangeably.

The term "yeast strain able to metabolize glucose" denotes in the sense of the invention a yeast strain capable of converting glucose into ethanol, i.e. capable of fermenting glucose. A yeast strain able to metabolize glucose within the meaning of the invention is a yeast strain that converts at least 70%, preferably at least 80%, and more preferably at least 90% of the glucose into ethanol in 60 hours in a fermentation medium comprising 150 g of glucose per kg of fermentation medium, in usual conditions for alcoholic fermentation.

Preferably, the method used to measure the percentage of glucose converted into ethanol is as follows:

The yeast strain used is inoculated in synthetic fermentation medium at 0.25 g of yeast in dry matter/kg of fermentation medium. The 60 hour duration is calculated from the inoculation of the fermentation medium with the yeast strain. A synthetic fermentation medium is a medium whose exact chemical composition is known. In the scope of the invention, a synthetic fermentation medium comprises a carbon source, a nitrogen source, a phosphorus source, and the essential vitamins and minerals for the growth of a yeast strain. Preferably, the fermentation medium used to measure the percentage of glucose converted into ethanol is YF as defined in the example embodiments (denoted YF Ac because of the presence of acetic acid).

The fermentation is typically conducted at a temperature comprised between 28 and 37° C., or between 30 and 35° C., advantageously equal to 32° C., with moderate stirring, for example at 90 or 100 rpm. The stirring is moderate so as to not be oxygenating. The pH of the medium is preferably controlled, for example by the buffering power of an acid/base pair (such as the acetic acid/acetate pair), and acid, advantageously comprised between 3.5 and 6, or 4 and 5.5, even more advantageously equal to 4.4 or 5.

The amount of ethanol present in the fermentation medium is measured by any appropriate means known to the person skilled in the art. It can be a direct measurement of the ethanol produced or an indirect measurement through a parameter correlated to ethanol production, such as $CO_2$ production determined by measuring the mass lost. For example, the production of alcohol may be measured by chromatography, including HPLC (High Performance Liquid Chromatography), an enzymatic kit (for example the determination of ethanol by Boehringer kit), or a determination by potassium dichromate. The amount of glucose in the fermentation medium is measured by any appropriate means known to the person skilled in the art, preferably by chromatography, in particular HPLC.

In the context of the invention, "organic acid" or "weak organic acid" is understood to mean a carboxylic acid that can inhibit the fermentation of a sugar, advantageously glucose. It advantageously involves acetic acid, levulinic acid, or formic acid, still more advantageously acetic acid.

It should be noted that it is known that only the non-dissociated or non-ionized form of such acids have inhibition ability. In the context of the invention, "un-ionized or non-dissociated form" of a carboxylic acid is understood as the protonated form thereof. In practice, the form of such organic acids depends on the pH of the medium in which they are incorporated. At a pH greater than the pKa of the acid, the acid will be mostly found in dissociated form or $COO^-$ ions. In contrast and at a lower pH, the majority form is the non-dissociated or unionized form (COOH). In the remainder of the invention, the quantities or concentrations stated refer to acetic acid added to the medium, containing dissociated and undissociated forms according to the pH of said medium.

The terms "resistant to an organic acid" or "acetic-acid resistant" denote a yeast strain that can ferment at least one sugar, particularly glucose, with the organic/acetic acid having limited impact on the alcoholic fermentation curve. The alcoholic fermentation curve representing the quantity of alcohol produced as a function of time generally includes three phases: a latency phase during which there is not ethanol production, an alcohol production phase, and a plateau phase, which corresponds to the end of the fermentation.

In a known manner, acetic acid inhibits glucose fermentation, this inhibition translating as a delay during initiation of fermentation with the kinetics subsequently remaining unchanged. It should be noted that in the presence of both glucose and xylose in the medium, yeast strains ferment glucose first because of catabolite repression.

Accordingly, an "acetic-acid resistant strain" advantageously delays the initiation of alcoholic fermentation by less than 30 hours, preferably less than hours, more preferably less than 15 hours, perhaps 10 hours. Preferably, reference is made to capacity to ferment glucose with a delay in initiation of alcoholic fermentation as indicated above.

The fermentation medium used to assess resistance to acetic acid is preferably a synthetic medium, more preferably the medium YFAc as illustrated in the embodiment examples. The composition of medium YFAc is as follows: 150 g/kg of glucose, 5 g/kg of yeast extract, 4.7 g/kg of DAP (diammonium phosphate), 11.4 g/kg of citric acid, 4 g/kg of acetic acid, 13.5 g/kg of sodium citrate, 1 mL/kg of Tween 80, 2 mL/kg of $ZnSO_4$ (at 10.6 g/L), 2.5 ml/kg of $MgSO_4$ $7H_2O$ (at 400 g/L), 1 mL/kg of thiamine (at 18.24 g/L), 1 mL/kg of pyridoxine (at 5.28 g/L), 1 mL/kg of biotin (at 1.76 g/L), 1 mL/kg of panthotenate (at 3.8 g/L), 2.5 mL/kg of nicotinic acid (at 8 g/L), 1 mL/kg of mesoinositol (at 50 g/L), 1 mL/kg of riboflavin (at 1 g/L), 1 mL/kg of para-aminobenzoate (at 1.2 g/L), pH adjusted to 4.4 with KOH. The inoculation of the yeast strain used to evaluate resistance to acetic acid is preferably 0.25 g dry matter/kg of fermentation medium. The time t=0 of the alcoholic fermentation corresponds to the time when the fermentation medium is inoculated with the yeast strain. Alcoholic fermentation should be conducted preferably at 32° C. under medium stirring, for example 90 rpm.

Note that at the concentration of 2000 ppm, acetic acid does not inhibit the fermentation. In a suitable manner, acetic acid is added at from 1 to 10 g/kg of fermentation medium, for example 4 g/kg of fermentation medium In the sense of the invention, "MCM7" denotes the gene coding the protein Mcm7p also called protein Cdc47p, and the product of the expression of this gene.

"Gene coding Mcm7p" or "MCM7 gene" are understood in the sense of the invention the gene of the yeast *Saccharomyces cerevisiae* located on chromosome II between the 625767 and 628304 positions, corresponding to ORF (Open Reading Frame) coding Mcm7p. These positions are indicated in reference to the genome of the yeast strain *S. cerevisiae* S288c, particularly its complete sequence, available in the databases under reference GenBank GCA_000146045.2. (version of Apr. 18, 2011), and whose NCBI reference is Gene ID: 852501. The sequence of chromosome II, used as a reference sequence for numbering, is that accessible under number NCBI NC_001134.7 (23 Dec. 2010; SEQ ID NO: 1).

The term "upstream of gene" must be understood in its generally accepted meaning in molecular biology, i.e. as meaning the region located at 5' (of the coding strand) of the initiation site for the gene transcription. In a classic manner, this region (also called "promoter/regulatory region") is involved in the expression of MCM7 gene, comprising in particular promoter and regulatory sequences, such as binding sites for transcription regulators. In the sense of the invention, this region is constituted of the 1200 5' nucleotides at the initiation site of the transcription of the gene encoding Mcm7p.

"Induction of the expression of MCM7 by or in the presence of an organic acid" or "overexpression of MCM7 by or in the presence of an organic acid," is understood in the presence of the invention to mean an increase in the level of expression of the gene encoding Mcm7p in the presence of organic acid, in comparison with the level of expression of this gene in the same strain in the absence of the organic acid. This increase in expression can translate to the nucleotide level (increased mRNA) or to the protein level. The person skilled in the art will therefore be able to choose the measurement method that seems the most appropriate to him and the simplest to implement among the well known methods of molecular biology and biochemistry (Northern blot, PCR, Western blot, etc.).

In the sense of the invention, the terms "induction of the expression of MCM7 mediated by the transcription factor Haa1p" or "overexpression of MCM7 mediated by the transcription factor Haa1p" mean that the induction of the expression or the overexpression of MCM7 targeted in the present application depend on transcription factor Haa1p. In other words, in the absence of transcription factor Haa1p, for example for the yeasts in which this gene is deleted or carries mutation(s) that make it non-functional, or even in conditions where the level of Haa1p is limited, yeasts are no longer capable of inducing the expression of MCM7, in particular in the presence of organic acid.

In the context of the invention, "Haa1p binding site" is understood to mean the nucleotide sequence recognized by the Haa1p transcription factor, allowing it to bind at the target gene whose transcription level is then regulated by Haa1p. According to Mira et al. (*Nucleic Acid Research*, 2011, 39 (16):6896-6907), the minimum motif recognized by Haa1 has the following sequence:

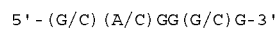

instead of motif-5'-GNN(G/C)(A/C)(A/G)G(A/G/C)G-3', determined previously in silico.

DETAILED DESCRIPTION OF THE INVENTION

According to a first aspect, the invention relates to the use of the MCM7 gene to confer resistance to an organic acid on or to a yeast strain.

According to an advantageous embodiment, the resistance conferred is resistance to acetic acid, whose presence in high concentrations in the lignocellulose hydrolysates is intrinsically related to that of acetyl groups associated in a covalent manner with the hemicellulose molecules.

According to another advantageous embodiment, the resistance to the organic acid in the yeast strain translates during the glucose fermentation, for which the delay in initiation of fermentation is lessened or reduced.

Advantageously, the use of the MCM7 gene is of interest when it is induced, advantageously in the presence of the organic acid in question, in particular of acetic acid.

Even more advantageously, the expression of the MCM7 gene induced by the presence of the organic acid is mediated by the transcription factor Haa1p. In an appropriate manner, the sequence upstream of the MCM7 gene comprises a binding site for Haa1p.

According to a specific embodiment, the sequence upstream of the MCM7 gene comprises the following sequence:

GAGGGG or

GAGGAGGGG or

SEQ ID NO: 2 or

SEQ ID NO: 3 or

SEQ ID NO: 4.

According to another embodiment, the sequence upstream of the MCM7 gene has at least one of the following characteristics:

a T at position 624536;
a T at position 624732;
a G at position 624736;
a C at position 624758;
a G at the 624794 position 624794;
an A at position 624801;
an A at position 624832;
a C at position 625073;
a G at position 625146;
an A at position 625199.

As already stated and in the scope of the invention, the position number corresponds to that of the reference strain S288c. Therefore "position" must be understood as the position, in the strain studied, that corresponds to the given position.

According to a preferred embodiment, the sequence upstream of the MCM7 gene has at least one G at position 624794. According to another embodiment, it has a C at position 624758, a G at position 624794 and an A at position 624801, or all of the characteristics set out above.

According to a preferred embodiment, the yeast strain targeted by the present invention belongs to the Hemiascomycetes group. Preferred strains belong to the *Saccharomyces*, *Pichia* and *Yarrowia* genera, advantageously *Saccharomyces*. Among *Saccharomyces*, it advantageously concerns *Saccharomyces cerevisiae*.

According to another feature, the invention concerns a selection process for a yeast strain resistant to an organic acid comprising:

the demonstrated induction of the expression of the MCM7 gene in the presence of the organic acid; and/or the demonstrated presence, at least at one allele of the strain, of a Haa1p binding site in the sequence upstream of the MCM7 gene, advantageously the sequence GAGGGG or GAGGAGGGG or SEQ ID NO: 2 or SEQ ID NO: 3 or SEQ ID NO: 4; and/or the demonstrated presence, at least at one allele of the strain, of the presence of a base G at position 624794 on chromosome II.

As already stated, the organic acid is advantageously acetic acid.

According to another preferred embodiment, the resistance to the organic acid of the resulting selected strain is observed during its glucose fermentation.

Accordingly, the present invention offers a genotypic screening method for strains of interest, here resistant to an organic acid. This approach is much less expensive, in terms of both time and money, than phenotypic screening traditionally used.

As set out, 3 criteria can be evaluated:

The first criterion consists in evaluating the strain's capacity to induce the expression of MCM7 in the presence of organic acid. As already stated, this induction of expression can be evaluated by any technique known to the person skilled in the art at the level of either the transcription or the protein.

The second criterion relies on the presence, at 5' of MCM7, of a Haa1p binding site. Accordingly, and in a suitable manner, the region located upstream of MCM7 comprises the sequence (G/C)(A/C)GG(G/C)G, perhaps GNN(G/C)(A/C)(A/G)G(A/G/C)G (where N is a nucleotide chosen from A, C, G and T).

According to a specific embodiment, this region contains at least one sequence chosen from:

GAGGGG corresponding to a minimum Haa1p binding site;

GAGGAGGGG corresponding to the motif recognized by Haa1p, determined in silico;

The sequence SEQ ID NO: 2;
The sequence SEQ ID NO: 3;
The sequence SEQ ID NO: 4;
advantageously the sequence SEQ ID NO: 3 or 4.

These sequences can be demonstrated by any technique known to the person skilled in the art such as sequencing, PCR, hybridization.

As is shown in the example embodiments, this may relate only to one allele of this strain, perhaps to several, perhaps even to all the alleles (two in the case of a diploid yeast).

According to a third criterion, the strain presents, at least at one allele, a base G at the position corresponding to the 624794 position of chromosome II, indicated in bold in the corresponding sequence in the minimum Haa1p binding site (GAGGGG). Note that an A is observed in this position in non-acetic-acid resistant strains. Without wanting to be bound by any category, the replacement of a base A by a base G allows the creation of a functional Haa1p binding site, allowing the induction of the expression of MCM7 in the presence of acetic acid.

Note that other mutations can be found in this region, advantageously chosen from:

a T at the 624536 position;
a T at the 624732 position;
a G at the 624736 position;
a C at the 624758 position;
an A at the 624801 position;
an A at the 624832 position;
a C at the 625073 position;
a G at the 625146 position;
an A at the 625199 position.

According to a specific embodiment, a strain targeted by the invention is selected because of the presence of at least one base G at the position corresponding to the 624794 position of chromosome II, perhaps of at least one C at the 624758 position, a G at the 624794 position and an A at the 624801 position, perhaps even because of the 10 nucleotides mentioned above in relation with the specific positions stated, at least in one of its alleles.

The demonstration or identification of these mutations is easily achieved by the person of skill in the art, for example by sequencing the positions of interest.

The interest of a strain identified using this method can of course be confirmed by a phenotypic approach, consisting of evaluating the capacity of the strain selected to ferment glucose in the presence of acetic acid, for example as described above.

These various genotypic screening criteria can also be implemented to produce or obtain yeast strains resistant to an organic acid, advantageously acetic acid, particularly in the context of glucose fermentation.

Accordingly and using the available molecular biology tools, it is possible to do mutagenesis (directed or random) on yeast strains to obtain the desired phenotype. As already stated, the presence of the genotypic characteristics stated above is only a priori necessary at one allele. Alternatively, this mutagenesis can therefore be achieved on spores (or segregants) that are then hybridized with other spores, optionally from another strain presenting another phenotypic trait of interest.

Advantageously, the invention proposes a method for obtaining a yeast strain resistant to an organic acid, based on a genotypic screening conducted in haploid spores or segregants.

Accordingly and according to another feature, the invention proposes a method for obtaining a yeast strain resistant to an organic acid comprising:

a sporulation step for two parental strains having different genomes or divergent phenotypic traits;

a mass hybridization step for the spores or segregants obtained, said process comprising at least one selection step of spores or segregants because of their capacity to induce the expression of MCM7 in the presence of organic acid and/or the presence of a Haa1p binding site in the sequence upstream of MCM7, advantageously the demonstration of the sequence SEQ ID NO: 3 or SEQ ID NO: 4, and/or the presence of a base G at the 624794 position of chromosome II.

In a characteristic manner, the method of the invention comprises a step of sporulation of the parental strains. This technique is well known to the person skilled in the art and does not therefore require further description. As an example, the sporulation step can be conducted by cultivating the parental strains in appropriate culture conditions, such as for example in a deprived medium.

Among the parental strains, at least one of them has the phenotype of interest, here resistance to an organic acid, advantageously acetic acid, in the sense of the invention. Advantageously, this delays initiation of alcoholic fermentation less than 30 h, preferably less than 20 hours, more preferably less than 15 hours perhaps 10 hours in the fermentation medium YFAc with an inoculum of 0.25 g of dry matter of yeast/kg of medium. Such strains are well known to the person skilled in the art. If need be, the person skilled in the art will be able to produce the parental yeast strain resistant to the organic/acetic acid in the sense of the invention, for example by the usual techniques using selection pressure.

Note that a parental strain of interest can also be identified using a selection method, the subject-matter of the present invention.

In the specific case of the use of S. cerevisiae, it may in particular be strain EGAc1 filed under the Budapest treaty at the CNCM (Collection Nationale de Cultures de Microorganismes, Institut Pasteur, 25 rue du Doctor Roux, 75724 Paris Cedex 15) under number I-4839 on Mar. 13, 2014.

As shown in the context of the present application, where this phenotypic trait is optionally carried by only one allele, sporulation gives rise to spores not bearing this genotypic trait, here half of the spores in the case of a diploid parental strain bearing only one allele with resistance to organic/acetic acid.

In a specific case, the two parental strains used in the context of the method of the invention have a phenotype of resistance to an organic acid in the sense of the invention.

In a suitable manner, at least one of the parental yeast strains, particularly that resistant to organic/acetic acid, advantageously both parental strains, can ferment glucose in the sense of the invention.

According to a preferred embodiment, the second parental yeast strain, advantageously the one not having resistance to organic/acetic acid, has a second phenotypic trait of interest. This is for example the capacity to metabolize pentoses, particularly glucose present in large quantities in lignocellulose hydrolysates.

Accordingly, yeast strains that can ferment glucose and also metabolize pentoses are available:

As an example, document WO 2010/000464 reports obtaining yeast strains able to ferment pentoses because of a bacterial gene coding for a xylose isomerase (XI) which converts xylose into xylulose which can be metabolized by the yeast. As an alternative, a eukaryotic pathway should be noted comprising xylose reductase (XR or XYL1) generating xylitol and a xylitol dehydrogenase (XDH or XYL2) that can also produce xylulose.

Thus, document WO 2012/072793 describes improved yeast strains combining exogenous genes coding a xylose isomerase and a xylitol dehydrogenase with which to eliminate xylitol which proves to be an inhibitor of xylose isomerase. Such strains, in particular the strain registered under the Budapest treaty with the CNCM (Collection Nationale de Cultures de Microorganismes) on Oct. 5, 2011 under number I-4538, have improved yields and therefore proven industrial utility for the production of ethanol.

In that respect and according to a specific embodiment, a second parental strain used in the context of the method of the invention is the strain registered under the Budapest treaty with the CNCM (Collection Nationale de Cultures de Microorganismes, Institut Pasteur, 25 rue du Doctor Roux, 75724 Paris Cedex 15) under number I-4538 on Oct. 5, 2011.

The method of the invention further comprises a mass hybridization step for the spores or segregants obtained.

This step is easily carried out according to conventional methods used in the field and described in detail in chapter 7 "Sporulation and Hybridization of Yeast" by R. R. Fowell, in the reference work "The Yeasts", Volume 1, edited by A. H. Rose and J. S. Harrison, 1969-Academic Press. In brief, the hybridization is achieved by adding the spores in question to a suitable culture in the hybridization step. Typically, the person skilled in the art will be able to use for this step complete culture medium of the YPG type (containing 10 g/L yeast extract, Bactopeptone 20 g/L, glucose 20 g/L and demineralized water qsp 1 L).

The selection step for spores or segregants of interest achieved as described previously on the basis of at least one of the following 3 criteria:

The first criterion consists in evaluating the spore's capacity to induce the expression of MCM7 in the presence of organic acid. As already stated, this induction of expression can be evaluated by any technique known to the person skilled in the art at the level of either the transcription or the protein. It must be understood that this step consists in positively selecting the spores or segregants having this phenotype (induction of expression of MCM7 by an organic acid, advantageously acetic acid) i.e. in isolating spores having this phenotype for the next step.

The second criterion relies on the presence, at 5' of MCM7 of the spore, of a Haa1p binding site. Accordingly, and in a suitable manner, the region located upstream of MCM7 comprises the sequence (G/C)(A/C)GG(G/C)G, perhaps GNN(G/C)(A/C)(A/G)G(A/G/C)G (where N is a nucleotide chosen from A, C, G and T).

According to a specific embodiment, this region contains at least one sequence chosen from:
GAGGGG corresponding to the minimum Haa1p binding site;
GAGGAGGGG corresponding to the motif recognized by Haa1p, determined in silico;
The sequence SEQ ID NO: 2 or
The sequence SEQ ID NO: 3 or
The sequence SEQ ID NO: 4)
advantageously the sequence SEQ ID NO: 3 or 4.

These sequences can be demonstrated by any technique known to the person skilled in the art such as sequencing, PCR, hybridization.

According to another criterion, the spore has a base G at the position corresponding to the 624794 position of chromosome II, indicated in bold in the corresponding sequence in the minimum Haa1p binding site (GAGGGG). Note that an A is observed in this position in non-acetic-acid resistant spores. Without wanting to be bound by any category, the replacement of a base A by a base G allows the creation of a functional Haa1p binding site, allowing the expression or overexpression of MCM7 in response to acetic acid.

Note that other mutations can be found in this region, advantageously chosen from:
a T at the 624536 position;
a T at the 624732 position;
a G at the 624736 position;
a C at the 624758 position;
an A at the 624801 position;
an A at the 624832 position;
a C at the 625073 position;
a G at the 625146 position;
an A at the 625199 position.

According to a specific embodiment, a segregant targeted by the invention is selected because of the presence of at least one base G at the 624794 position of chromosome II, perhaps of at least one C at the 624758 position, a G at the 624794 position and an A at the 624801 position, perhaps even because of the 10 nucleotides mentioned above in relation with the specific positions stated.

The demonstration or identification of these mutations is easily achieved by the person of skill in the art, for example by sequencing the positions of interest.

A selection like this can for example be made on the basis of total or partial sequencing according to the techniques of molecular biology well known to the person of skill in the art, or by PCR techniques. The sequencing can accordingly be achieved by sequencing by hybridization or by high throughput sequencing techniques such as pyrosequencing, synthetic sequencing or ligation sequencing. Alternatively, the selection can be made on the basis of PCR techniques by looking for the targeted polymorphisms. In this context mention may be made of, for example, multiplex PCR techniques, which will look for several polymorphisms in a single test, nested PCR, which produces highly sensitive results, or colony PCR, which does not require DNA extraction.

To achieve the sequencing or PCR, a DNA multiplication step may be necessary, to have sufficient biological material available. It will then be possible to proceed with amplification by cultivating each strain or spore in a culture medium suitable for its reproduction. Further, a DNA extraction step for yeasts may be necessary, and can be done according to molecular biology methods well known in the field of the invention.

The method of the invention can be implemented in diverse ways: the yeast selection step can be done from parental strains, and/or from spores that come from it, and/or from strains obtained after hybridization. As already stated, it is however particularly advantageous to proceed with the selection step from spores coming from the parental strains.

Thus, according to one preferred embodiment, a method according to the invention comprises the following steps:
a) prepare segregants from a first parental strain and segregants from a second parental strain;
b) select from among the segregants of step a) those that can induce the expression of MCM7 in the presence of organic acid and/or having a Haa1p binding site in the sequence upstream of MCM7, advantageously the sequence SEQ ID NO: 3 or SEQ ID NO: 4, and/or having a base G at the 624794 position of chromosome II;
c) hybridize the segregants from the first parental strain and selected in step b) with segregants from the second parental strain, optionally selected in step b);
d) select among the hybrids from step c) those resistant to organic acid.

Step a) of the method corresponds to a preparation step for segregants from two different parental yeast strains, advantageously *S. cerevisiae*, i.e. a sporulation step. The person skilled in the art will easily be able to obtain segregants from parental strains defined above, according to the methods well known in the field of the invention.

In an advantageous embodiment, this step comprises the culture of the first parental yeast strain firstly and the second parental yeast strain secondly, in a medium deprived of nitrogen or sugar.

In a preferred manner, the parental strains used are yeast strains belonging to the *Saccharomyces* group, advantageously *Saccharomyces cerevisiae*.

According to a preferred embodiment, the first strain is chosen for its resistance capacity to organic acid, advantageously acetic acid, particularly during glucose fermentation. It may in particular be strain EGAc1 registered under the Budapest treaty with the CNCM under number I-4839 on Mar. 13, 2014. The segregants of this strain will as a priority be the subject of the selection step b) of the method.

According to another preferred embodiment, the second parental yeast strain is chosen for another phenotypic trait of interest, for example its capacity to metabolize xylose. It can for example be the strain registered under the Budapest treaty with the CNCM under number I-4538 on Oct. 5, 2011.

In a specific case, the second parental yeast may also have resistance capacity to organic acid, advantageously acetic acid, particularly during glucose fermentation. In that case, the spores of this strain will also be the subject of the selection step b) of the method.

Step b) of the method of the invention is used as described and allows the removal of spores that do not have the desired phenotypic trait, here resistance to an organic acid in the sense of the invention. Accordingly and thanks to this step, the probability of obtaining from the hybridization a strain having this phenotypic trait is greatly increased.

Step c) of the method of the invention is a step of hybridization of segregants from a first parental yeast strain with segregants from a second parental strain, where at least one of the segregant populations has been previously selected in step b), advantageously that from the first parental yeast strain.

Preferably, a mass hybridization is conducted in step c). In other words, step c) corresponds preferably to a hybridization step for all of the spores from step b).

Optional step d) of the method consists in selecting among the hybrids from step c) those capable of alcoholic fermentation and having a phenotype of resistance to organic acid, advantageously acetic acid. As already stated, this step is easily achieved by traditional selection methods, using usual culture techniques. This step is advantageously used on a medium comprising glucose.

The present invention is going to be illustrated more ahead using the following example embodiments, supported by the attached figures. However, they have no limiting scope.

LEGENDS FOR THE FIGURES

FIG. 1 shows the flow chart used to determine the proportion of alleles from EGAc1 (I-4839) in yeast populations that fermented in the presence of acetic acid (popB) or in yeast populations that fermented without acetic acid (popC) and along all of chromosome II.

S288c: strain of *S. cerevisiae* whose genome serves as GenBank reference GCA_000146045.2., version of Apr. 18, 2011; NCBI Gene ID: 852501; chromosome II: NCBI NC_001134.7)

EGAc1: strain registered under the Budapest treaty with the CNCM (Collection Nationale de Cultures de Microorganismes, Institut Pasteur, 25 rue du Doctor Roux, 75724 Paris Cedex 15) on Mar. 13, 2014, under number I-4839.

I-4538: strain registered under the Budapest treaty with the CNCM (Collection Nationale de Cultures de Microorganismes, Institut Pasteur, 25 rue du Docteur Roux, 75724 Paris Cedex 15) under number I-4749.

EGAc2: strain registered under the Budapest treaty with the CNCM (Collection Nationale de Cultures de Microorganismes, Institut Pasteur, 25 rue du Doctor Roux, 75724 Paris Cedex 15) on Mar. 13, 2014, under number I-4840.

(B) the LOD score value (similarity index) as a function of the position along chromosome II for the 3 series of experiments conducted.

Figure 4:
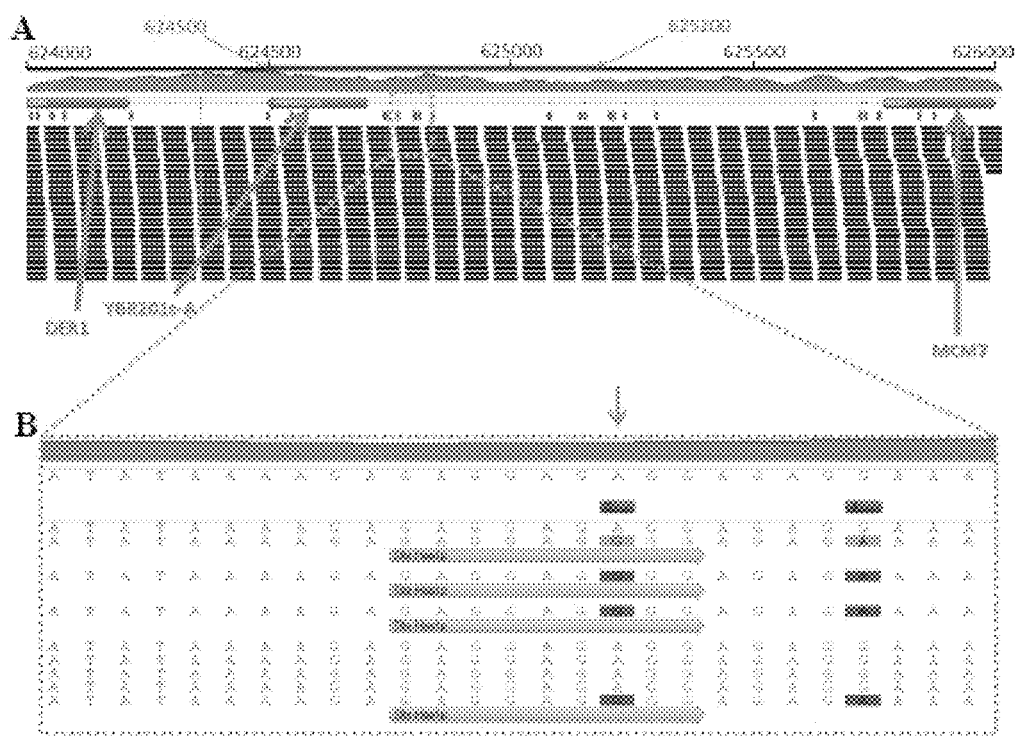

FIG. 4 corresponds to (A) a graphic representation of assembly of genome reads for strain EGAc2 (I-4840) in the 624000 to 626000 bp area of chromosome II of the reference strain. The area where the LOD scores are the highest is shown (624500 to 625200 bp; SEQ ID NO: 3).

(B) a focus on the impact of SNP (A>G) that affects 50% of the alleles in this strain in the 624794 position. The arrows represent the presence of a site recognized by the Haa1p transcription factor in the sequence SEQ ID NO: 2.

Figure 5:
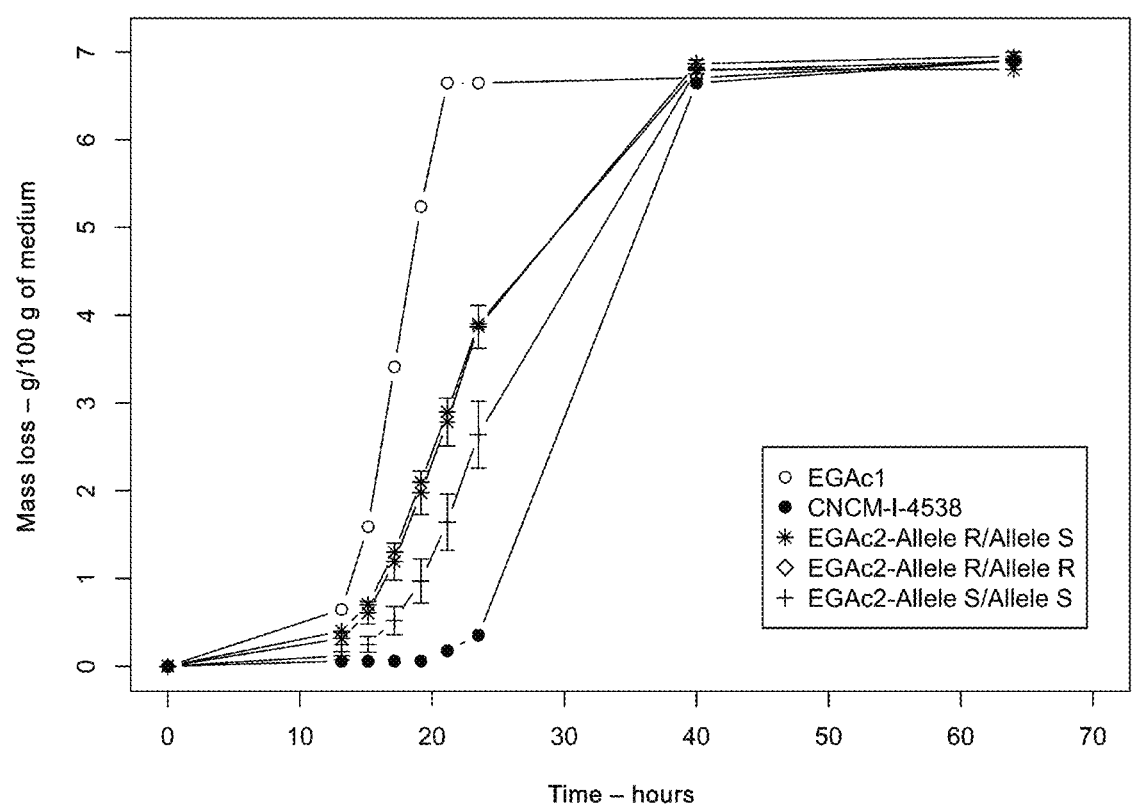

FIG. 5 relates the average change in mass loss during a fermentation on YFAc medium at 32° C. with an inoculum of 0.25 g/kg (dry matter eq.). The strains used are:
strain I-4538, sensitive to acetic acid (S);
strain EGAc1 (I-4839), acetic-acid resistant (R);
strain EGAc2 (I-4840) heterozygous, denoted "EGAc2-AlleleR/AlleleS";
strain EGAc2 (I-4840) made homozygous for the allele from EGAc1 (resistant allele) at locus II-624794, denoted "EGAc2-AlleleR/AlleleR";

strain EGAc2 (I-4840) made homozygous for the allele from I-4538 (sensitive allele) at locus II-624794, denoted "EGAc2-AlleleS/AlleleS".

The error bars correspond to standard deviations calculated on the basis of measurements made with the 7 homozygous strains for the resistant allele and the homozygous strains for the sensitive allele.

EXAMPLE EMBODIMENTS

Example 1: Identification of Genetic Traits and Mutations Related to the Phenotype of Resistance to Weak Organic Acids Such as Acetic Acid In these first experiments, the goal is to produce a diverse yeast population from a genetic point of view (a), so as not only to select the strains resistant to weak organic acids but also to be able to analyze the genetic traits involved in this phenotype (b).

a. Production of a Yeast Population Comprising Strains Resistant to Weak Organic Acids:

The yeast population was obtained by random recombination from mass sporulation and hybridization. This strategy is inspired by the work of Leo Parts et al. (2011, *Genome Res*, 21(7):1131-8). In brief, a segregant (also called spore) for an acetic-acid resistant strain (strain EGAc1/I-4839) is crossed with another segregant, from strain I-4538, thereby creating a first hybrid (strain EGAc2/I-4840), as described in WO2013/178915.

Secondly, the genome of strain EGAc2 (I-4840) was recombined randomly to obtain a very diverse yeast population from a genetic point of view. In practice, hybrid EGAc2 (I-4840) was set to sporulate then the spores obtained were left to freely rehybridize among themselves, as described in WO2013/178915. The cycle was reproduced 4 times, thereby generating a 24 reduction in the genetic distance in centiMorgan (cM).

b. Selection of Strains Resistant to Weak Organic Acids:

Strains resistant to weak organic acids were selected following the principles of population genetics, particularly the Hardy-Weinberg principle, which states that in an isolated population with unlimited count, not subject to selection, and in which there are no mutations, allele and genotype frequencies remain stable from generation to generation.

Accordingly, in the absence of selection, in the case of 2 alleles "A" and "B," where only "A" can play a role in adapting the population at a given selection pressure (for example resistance to weak organic acids), the frequencies of allele "A" and allele "B" in the population remain stable. By contrast, if the environment changes, and the medium is enriched with weak organic acid, then the less adapted strains will disappear (B) for the benefit of the more adapted strains (A). According to this principle, in the case where selection pressure exists, we then observe a deviation in this equilibrium over several generations. Accordingly, by comparing the allele frequency variations between a population not subjected to the selection and a population subjected to a selection pressure, one can determine the alleles that may be involved in the resistance or adaptation to the selection applied.

In practice, to have a control population, a sample of the population obtained in point a) was cultivated in a medium devoid of acetic acid (no selection pressure). The resulting population is called "population C."

In parallel, a sample of the population obtained in point a) was subjected to a high selection pressure by adding acetic acid at the start of the alcoholic fermentation in the presence of glucose. The resulting population is called "population B." In practice, acetic acid was added to the culture medium so as to obtain a concentration of 4 g/L.

c. Determination of Genetic Traits Involved in the Phenotype for Resistance to Weak Organic Acids:

Strain EGAc1 (I-4839) being acetic-acid resistant, it is expected that the genetic traits associated with this resistance are present in this strain. Consequently, to limit the number of alleles to analyze, one firstly identifies the alleles specific to strain EGAc1 (I-4839) that are present in strain EGAc2 (I-4840), and in populations C and B. Secondly, it is possible to determine the frequency of each of these alleles appearing in the stressed (B) or unstressed (C) populations.

The study of allele frequency variations along the genome was conducted in the following manner:

After the fermentations, the genomic DNA coming from strain EGAc1 (I-4839), from strain EGAc2 (I-4840) and from populations B and C were extracted then sequenced by the "Paired End" method using an Illumina HiS eq 2000.

Figure 1:
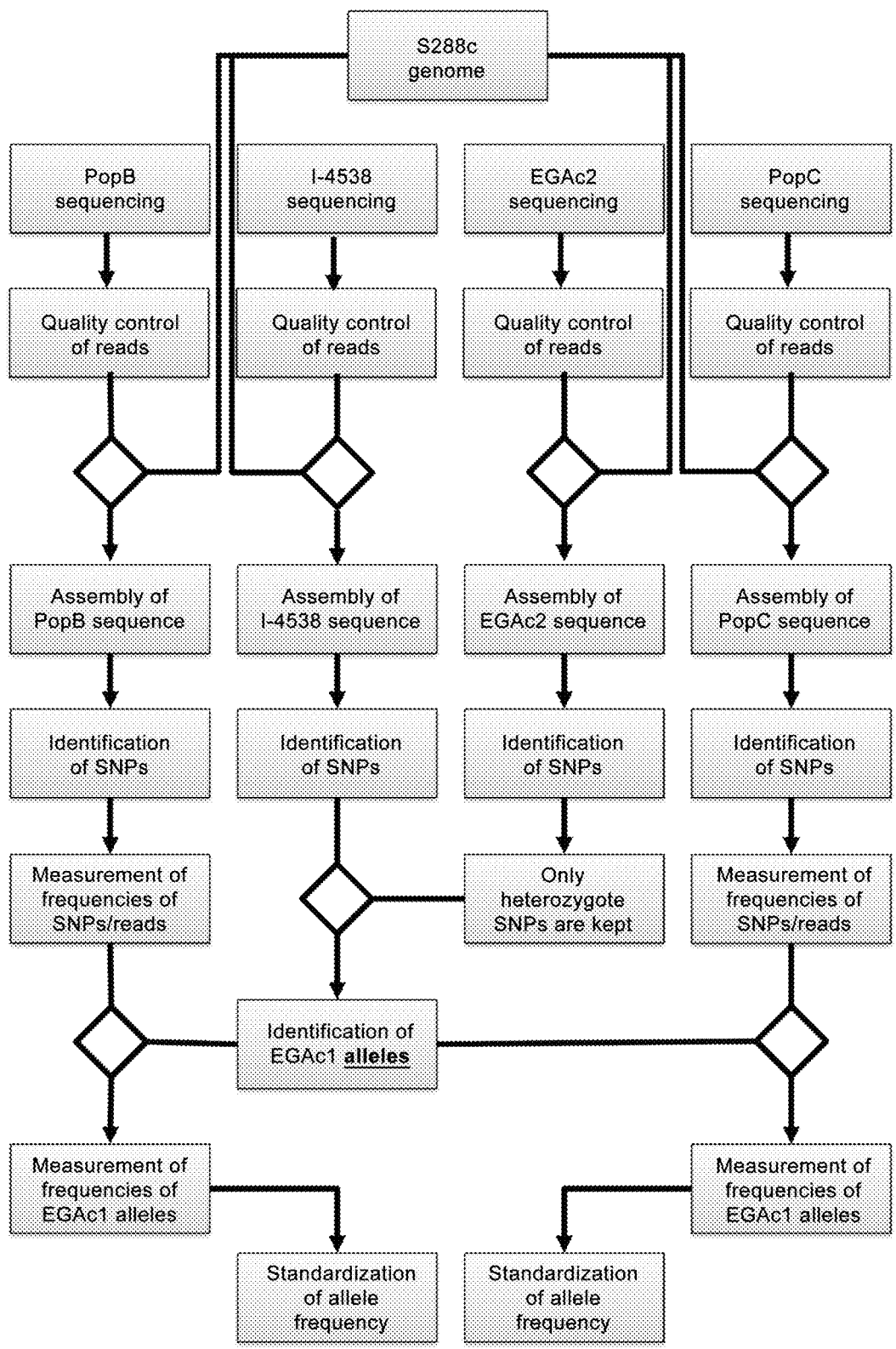

The results were then processed according to the approach illustrated in FIG. 1. Note that the reference genome is that for strain S288c (GenBank GCA_000146045.2., version of Apr. 18, 2011; NCBI Gene ID: 852501; NCBI NC_001134.7).

In the case of a study conducted on complex populations, the allele frequency reflects the number of individuals carrying the allele in question. So as an example and in direct application of the Hardy-Weinberg principle, if an allele is present with a frequency of 70%, it is possible to deduce that 91% of individuals in the population carry at least one copy of this allele.

Figure 2:
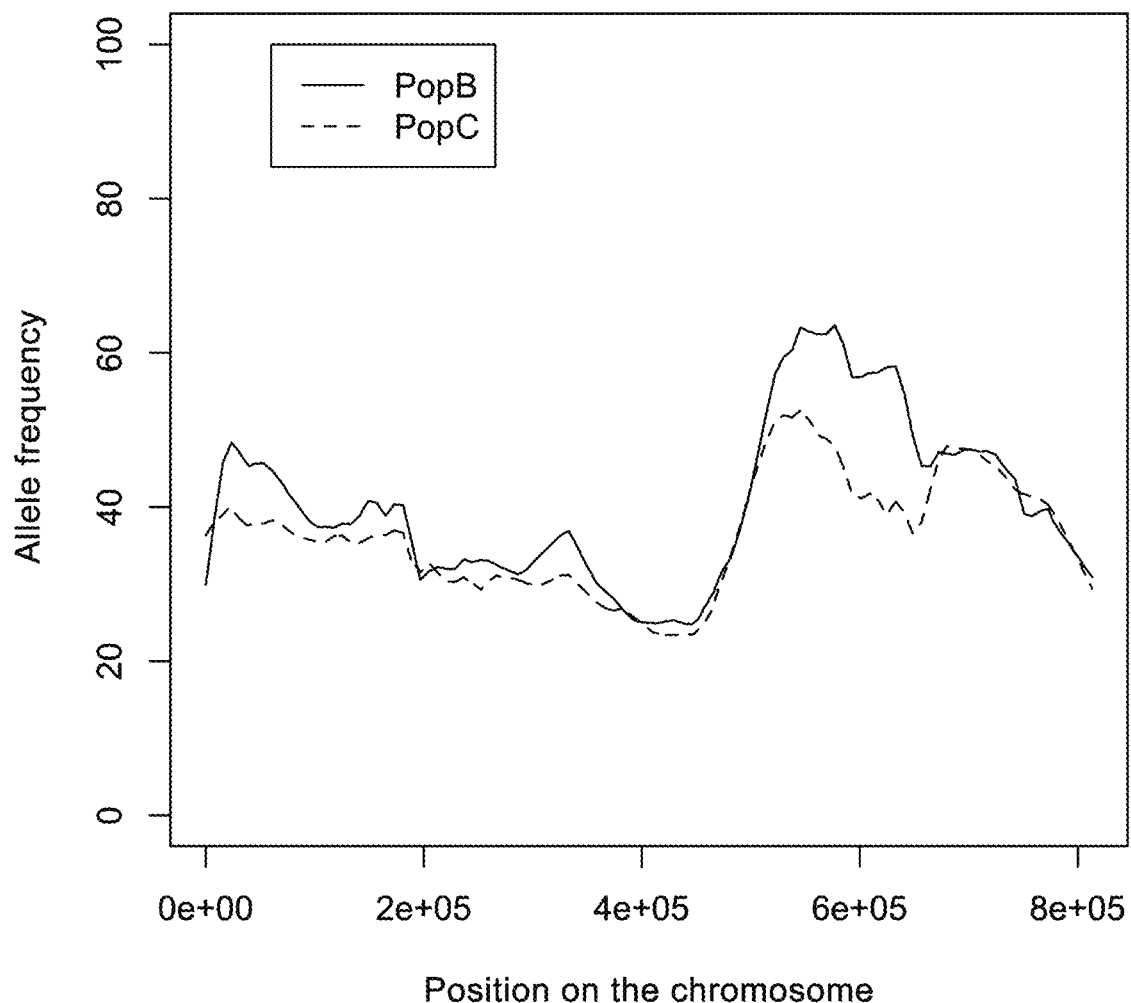
FIG. 2 shows the frequency averages for alleles in strain EGAc1 (I-4839) in both populations: PopC=not stressed, dotted; PopB=stressed, line

FIG. 2 shows how the allele frequency from strain EGAc1 (I-4839) changes along chromosome II and present in populations B and C.

The results in FIG. 2 show that in the first portion of chromosome II, the allele frequencies from EGAc1 (I-4839) are very close in both types of populations and up to about 530 kb. This observation suggests that the genes present in this part of chromosome II (from 0 to 530 kb) would not be involved in the acetic-acid resistance process transmitted by the segregant from strain EGAc1 (I-4839) to strain EGAc2 (I-4840).

The second part of chromosome II (from 530 kb to 660 kb) shows a dissociation in curves corresponding to allele frequencies from EGAc1 (I-4839) in both types of populations. This result shows that there is an allele that is more represented in the populations subjected to selection pressure than in those that fermented without this pressure. This overrepresentation suggests that this allele from EGAc1 (I-4839) would favor the multiplication of cells in the presence of acetic acid. In other words, the second part of chromosome II (from 530 kb to 660 kb) is identified as being a quantifiable genetic trait (also called QTL), i.e. a genetic region involved in acetic-acid resistance.

QTL are generally large sequences. One sub-region seems to stand out: this is the region from bases 624000 to 626000 of chromosome II. This region seems to include the highest allele frequency variations. Next, it is this sub-region that was analyzed.

d. Analysis of Genetic Traits Involved in the Phenotype for Resistance to Weak Organic Acids:

Within the QTL, these are more specifically frequency variations for punctual polymorphisms (SNP for "Single-Nucleotide Polymorphism"), in comparison with the strains that do not present the phenotypic trait studied, which can be the most relevant.

The base pair region 624000 to 626000 of chromosome II was therefore analyzed in more detail. The similarity index values for the SNPs that it comprises were analyzed to target the region comprising the most relevant SNPs in the phenotype for resistance to weak organic acids (i). Once this region was identified, the SNPs that it comprises were analyzed more deeply (ii).

i. Determination of the Most Region the Plus Pertinente:

The approach chosen was that of LOD scores, as described by Lander and Botstein (1989, *Genetics*, 121:185-99).

The first step consists in determining the inference:

$$fB = \frac{n1,B}{n1,B + n2,B}$$

$$fC = \frac{n1,C}{n1,C + n2,C}$$

In the first equation, "n1" is the number of reads bearing the SNP from strain EGAc1 (I-4839) in population B and "n2" the number of reads bearing the other SNP. The next equation relates to the same calculation but applied to the results of unstressed populations.

The second step consists in calculating the similarity:

The similarity (L) is defined as being a conditional probability function. Accordingly, this is the probability of having the allele of strain EGAc1 (I-4839), either in the population that fermented in the presence of acetic acid, or in the population that did not ferment in the presence of acetic acid, calculated according to the equations below:

$$\mathcal{L}_{(B|fB)} = \Pi_{i=1}^{3}(B_i|fB)$$

$$\mathcal{L}_{(C|fC)} = \Pi_{i=1}^{3}(C_i|fC)$$

The third step consists in calculating the LOD score:

From these determinations of similarity for each allele, it is now possible to calculate the LOD for each SNP and to combine it with the allele from strain EGAc1. The equation used is that published by Lander and Botstein in 1989:

$$LOD = \log\left(\frac{L(B \mid fB) \cdot L(C \mid fC)}{L(B \cup C \mid f)}\right)$$

Figure 3:
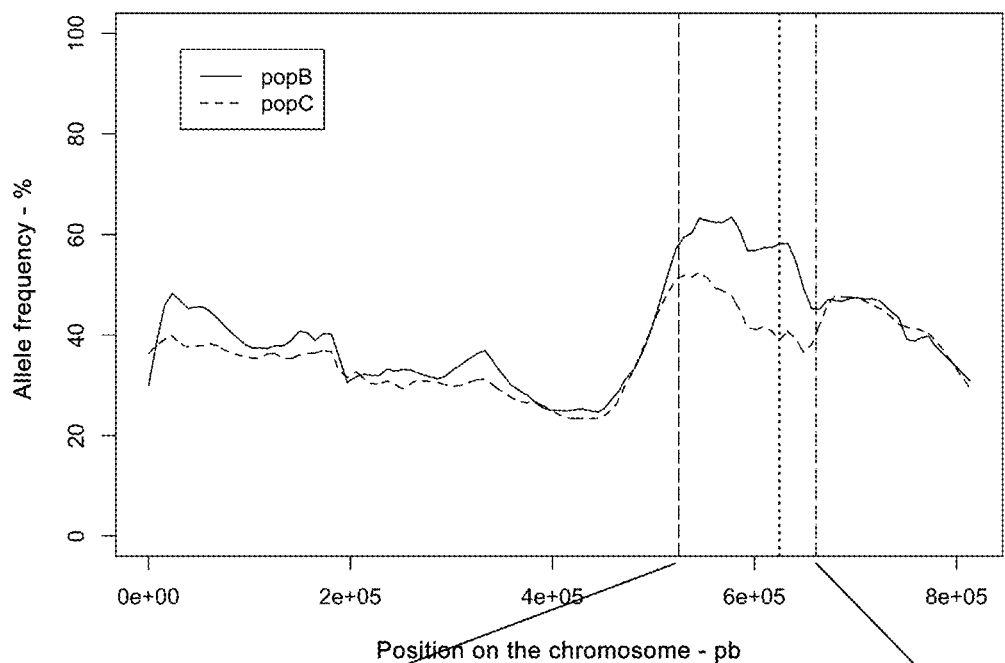
FIG. 3 shows (A) the frequency averages for alleles in strain EGAc1 (I-4839) in the yeast populations that fermented in the presence of acetic acid (popB: stressed, line) or in the yeast populations that fermented without acetic acid (popC: not stressed, dotted) and along all of chromosome II.
Figure 3:
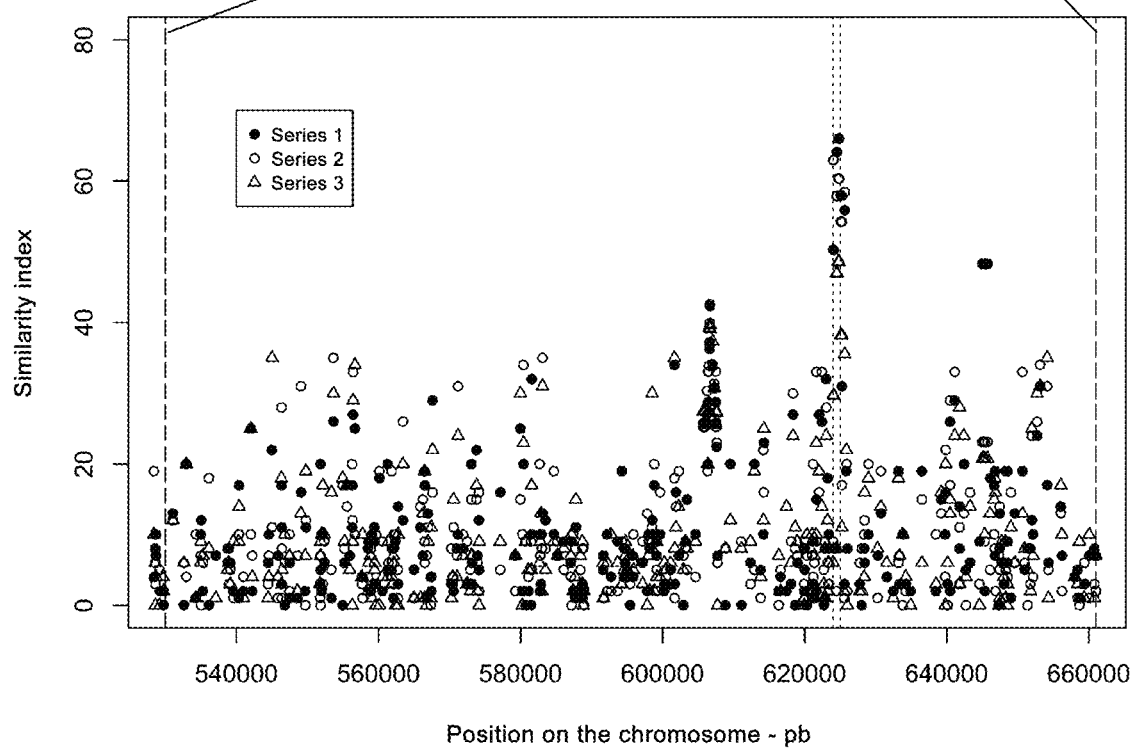

The LOD score was analyzed 3 times on the area of interest for chromosome II (3 independent experiments). These results are shown in FIG. 3. These results show that when the difference in allele frequency is high, the dispersion of LOD scores is also high (principally because of their mathematical and biological links).

FIG. 3B shows that an area comprised between 624500 bp and 625200 bp has high LOD scores that appear reproducible. The most relevant region identified is therefore the area between 624500 bp and 625200 bp of chromosome II (SEQ ID NO: 3).

ii. Analysis of SNPs in the Most Relevant Region (Between 624500 bp and 625200 bp of Chromosome II):

The genetic structures present and the SNPs found most frequently in the area considered (between 624500 bp and 625200 bp of chromosome II) in strain EGAc2 (I-4840) were analyzed.

These results are shown in FIG. 4.

10 SNPs were identified in the area between 624500 bp and 625200 bp (SEQ ID NO: 3) of chromosome II:

| Position (with reference to strain S288c: NC_001134.7; SEQ ID NO: 1) | Base in the reference strain | Mutation |
| --- | --- | --- |
| 624536 | A | T |
| 624732 | C | T |
| 624736 | A | G |
| 624758 | T | C |
| 624794 | A | G |
| 624801 | G | A |
| 624832 | C | A |
| 625073 | T | C |
| 625146 | C | G |
| 625199 | C | A |

The impact of these SNPs on the sequence of coding areas (open reading frames) did not show mutations causing changes to the protein sequence.

By contrast, polymorphism (A→G) in the 624794 position, which affects 50% of the alleles in strain EGAc2 (I-4840), reconstitutes a site recognized by the Haa1p transcription factor located upstream of MCM7, and codes a DNA helicase. DNA helicases replicate DNA and therefore regulate the cell cycle progression and, consequently, the production of biomass. In other words, yeasts having this SNP have a binding site for Haa1p transcription factor that the other yeasts do not have, upstream of a gene known to play an important role in cellular division. Accordingly, the fact that the presence of a site recognized Haa1p upstream of MCM7 makes the strains more resistant could hold to the fact that in the presence of acetic acid, yeasts carrying this site would multiply more quickly.

Example 2: Validation of the Interest of the Allele Denoted "EGAc1-II-624794"

To take another approach to analyzing the identified area of interest (particularly bearing mutations T→C in the 624758 position, A→G in the 624794 position and G→A in the 624801 position; SEQ ID NO: 4), it was chosen to achieve the loss of heterozygosity in strain EGAc2 (I-4840). Secondly, the performances of strains made homozygous for one or other of the two alleles were compared.

a) Construction of Homozygous EGAc2 Strains for the Wild Allele or for the Allele Comprising the SNP Identified as of Interest:

Strain EGAc2 (I-4840) is heterozygous for the QTL identified as of interest, i.e. bearing the SNP (A→G) in the 624794 position. Indeed, it has an allele denoted "II-624794" of strain EGAc1/I-4839 (i.e. having a G in the 624794 position) and an allele "I4538-II-624794" from strain I-4538 (i.e. having an A in the 624794 position). As a reminder, strain EGAc1 (I-4839) is acetic-acid resistant whereas strain I-4538 is not.

To better study the role of this mutation, homozygous strains either for allele II-624794 of strain EGAc1 (denoted "EGAc1-II-624794") or for allele II-624794 of strain I-4538 (denoted "I4538-II-624794") were prepared. To do this, a cassette called LOH was used. In its principle, the cassette LOH is constituted of a gene (KanMX4) conferring resistance to geneticin to yeasts that express it. Another part of the cassette carries the sequence GIN11m86. The latter is toxic for cells that express it (Akada et al., 1997, *Mol Gen Genet* 254, 267-74; Kawahata et al., 1999, *Yeast*, 15, 1-10 and Akada et al., 2002, *Yeast*, 19, 393-402). This system is qualified as dominant negative because a single copy of this sequence is necessary to confer the lethal genotype on the cells. In so far as the sequence GIN11m86 is placed under the dependence of promoter GAL2, it is possible to select on YNB+Galactose the cells that would have lost the cassette.

The strategy used to build homozygous EGAc2 strains for allele II-624794 is as follows:

The LOH cassette was flanked by recombinogenic sequences capable of deleting one of the two alleles. The selection of transformants is conducted on a YNB-G418 medium (containing geneticin). To determine which of the two alleles was kept, the locus was amplified by PCR using seeds, called validation seeds, outside the LOH cassette. The smallest of the resulting PCR fragments (650 bp) was cloned in a plasmid pTOPO then sequenced, from which it was determined which of the two alleles was kept. The strains were retransformed with a sequence identical to the allele kept. The new transformants were selected on a YNB medium containing galactose as only carbon source, allowing the selection of those that lost the LOH cassette. Finally, using validation seeds, PCR was again done. The product of this reaction is unique and was directly sequenced.

Using this strategy, 7 homozygous EGAc2 strains for allele "EGAc1-II-624794" (conferring resistance to acetic acid), denoted "EGAc2-AlleleR/AlleleR", and 5 homozygous EGAc2 strains for the allele denoted "I4538-II-624794" (conferring sensitivity to acetic acid), denoted "EGAc2-AlleleS/AlleleS", were built and validated.

b) Analysis of the Impact of Homozygosity on Resistance to Acetic Acid:

After having obtained the 12 previously cited homozygous strains, their capacity to ferment glucose in the presence of acetic acid was tested. These performances were measured on a YFAc medium (4000 ppm; pH 4.4), defined as follows:

| | |
| --- | --- |
| Glucose | 150 g/kg |
| EXL type J100 (Yeast extract) | 5 g/kg |
| DAP (Diammonium phosphate) | 4.7 g/kg |
| Citric acid | 11.4 g/kg |
| Na citrate (sodium citrate) | 13.5 g/kg |
| Acetic acid | 4 g/kg |
| Tween 80 | 1 mL/kg |
| $ZnSO_4$ 10.6 g/L; | 2 mL/kg |
| $MgSO_4$ $7H_2O$ 400 g/L; | 2.5 mL/kg |
| Thiamine 18.24 g/L; | 1 mL/kg |
| Pyridoxine 5.28 g/L; | 1 mL/kg |
| Biotin (1.76 g/L) + KOH | 1 mL/kg |
| Pantothenate (3.8 g/L) | 1 mL/kg |
| Niacin (8 g/L) | 2.5 mL/kg |
| Myo-inositol (50 g/L) | 1 mL/kg |
| Riboflavin (1 g/L) | 1 mL/kg |
| para-Aminobenzoate (1.2 g/L) | 1 mL/kg |

The mass loss results observed during the fermentation on this medium are shown in FIG. 5. The curves shown are the averages of the values obtained for all strains in the same genotype.

The results presented in FIG. 5 show that strains EGAc2 made homozygous for the sensitive allele (S) at locus II-624794 have a delay initiation in fermentation by more than EGAc2 strain (I-4840) on YFAc. This shows that the loss of allele "EGAc1-II-624794" in a strain EGAc2 for the benefit of a homozygosity of allele "I4538-II-624794" makes the strains obtained more sensitive to acetic acid during the glucose fermentation.

By contrast, the EGAc2 strains made homozygous for allele "EGAc1-II-624794" at locus II-624794 have fermentation kinetics on this medium that is not different than that of EGAc2 strain (I-4840). This result suggests that the homozygosity does not add anything to the strains in this medium.

In conclusion, this work reveals that the allele "EGAc1-II-624794" does indeed contribute to resistance to strain EGAc2 (I-4840) regarding acetic acid. However, a single copy seems to be sufficient to confer a resistance phenotype on acetic acid.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10738329B2). An electronic copy of the "Sequence Listing" will also be available from the USPTO upon request and payment of the fee set forth in 37 CFR 1.19(b)(3).

The invention claimed is:

1. A method of producing alcohol, the method comprising fermenting glucose using a *Saccharomyces* strain in which expression of the MCM7 gene is induced in the presence of acetic acid and/or that comprises a Haa1p binding site in the sequence upstream of the MCM7 gene and/or comprises a base G at position 624794 on chromosome II of the yeast genome.

2. The method according to claim 1, wherein the *Saccharomyces* strain comprises the sequence SEQ ID NO: 3 or SEQ ID NO: 4 upstream of the MCM7 gene.

3. A method for characterizing a *Saccharomyces* strain for resistance to acetic acid during glucose fermentation, comprising the following steps:
   detecting induction of MCM7 gene expression in the presence of acetic acid; and/or
   detecting the presence of a Haa1p binding site in the sequence upstream of the MCM7 gene in at least at one allele of the strain; and/or
   detecting the presence of a base G at position 624794 on chromosome II in at least at one allele of the strain.

4. A method for obtaining a *Saccharomyces* strain resistant to acetic acid during glucose fermentation, comprising the following steps:
   performing a sporulation step for a first parental *Saccharomyces* strain and a second parental *Saccharomyces* strain having different genomes to generate segregants;
   performing a mass hybridization step for the segregants obtained; and
   selecting segregants in which expression of MCM7 gene is induced by the presence of acetic acid and/or comprise a Haa1p binding site in the sequence upstream of MCM7 and/or comprise a base G at position 624794 on chromosome II, thereby obtaining a *Saccharomyces* strain resistant to acetic acid during glucose fermentation.

5. The method according to claim 4, characterized in that it comprises the following steps:
   a) preparing segregants from a first *Saccharomyces* parental strain and segregants from a second parental *Saccharomyces* strain;
   b) selecting from among the segregants from step a) those in which expression of the MCM7 gene is induced by the presence of acetic acid and/or those having a Haa1p binding site in the sequence upstream of MCM7 and/or those having a base G at position 624794 on chromosome II;
   c) hybridizing the segregants from the first parental *Saccharomyces* strain selected in step b) with segregants from the second parental *Saccharomyces* strain, optionally selected in step b); and
   d) selecting among the hybrids from step c) those resistant to acetic acid.

6. The method according to claim 4, characterized in that the first parental *Saccharomyces* strain resists acetic acid and the second parental *Saccharomyces* strain exhibits another characteristic of interest.

7. The method according to claim 4, characterized in that the first parental *Saccharomyces* strain is the strain EGAc1 deposited at the CNCM under number I-4839 on Mar. 13, 2014 and the second parental *Saccharomyces* strain is the strain deposited at the CNCM under number I-4538 on Oct. 5, 2011.

8. The method according to claim 3, characterized in that the first parental *Saccharomyces* strain resists acetic acid on a medium comprising glucose.

9. The method of claim 3, wherein the Haa1p binding site in the sequence upstream of the MCM7 gene comprises the sequence set forth in SEQ ID NO: 3 or SEQ ID NO: 4.

10. The method of claim 4, wherein the Haa1p binding site in the sequence upstream of the MCM7 gene comprises the sequence set forth in SEQ ID NO: 3 or SEQ ID NO: 4.

11. The method of claim 6, wherein the second parental *Saccharomyces* strain metabolizes xylose.

12. The method according to claim 3 characterized in that the *Saccharomyces* strain is *Saccharomyces cerevisiae*.

13. The method according to claim 4 characterized in that the *Saccharomyces* strain is *Saccharomyces cerevisiae*.

14. The method according to claim 1 characterized in that the *Saccharomyces* strain is *Saccharomyces cerevisiae*.

* * * * *